United States Patent [19]
Shaw

[11] Patent Number: 5,964,766
[45] Date of Patent: Oct. 12, 1999

[54] BUTTRESS THREAD IMPLANT

[75] Inventor: Leon Shaw, Delray Beach, Fla.

[73] Assignee: Biolok International, Inc., Deerfield Beach, Fla.

[21] Appl. No.: 08/172,702

[22] Filed: Dec. 27, 1993

[51] Int. Cl.⁶ .................................................. F16B 35/04
[52] U.S. Cl. ............................................. 606/73; 411/411
[58] Field of Search .......................... 606/73; 411/411, 411/412, 414; 433/174

[56] References Cited

U.S. PATENT DOCUMENTS

| | | | |
|---|---|---|---|
| 4,468,200 | 8/1984 | Münch | 606/73 |
| 4,576,534 | 3/1986 | Barth et al. | 411/412 |
| 5,061,135 | 10/1991 | Pritchard | 411/411 |

FOREIGN PATENT DOCUMENTS

| | | | |
|---|---|---|---|
| 512307 | 8/1939 | United Kingdom | 411/411 |
| 85/04568 | 10/1985 | WIPO | 606/73 |

*Primary Examiner*—Michael Buiz
*Assistant Examiner*—Vy Quang Bui
*Attorney, Agent, or Firm*—M. K. Silverman

[57] ABSTRACT

A buttress-thread dental implant constitutes a rigid body including axially symmetric and radially uniform circumferential spiral pitch surfaces in the range or about 22 to about 28 of such pitch surfaces per axial inch. Above each pitch surface is a concave upper bevel surface which is longer than a lower bevel surface beneath each pitch surface. The intersection of each plane of each pitch surface with each plane of each lower bevel surface defines a total included bevel angle in the range of about 90 to about 1.30 degrees. The implant is also characterized by ratio of thread pitch to thread depth in the range of about 1.25:1 to about 1.40:1.

11 Claims, 1 Drawing Sheet

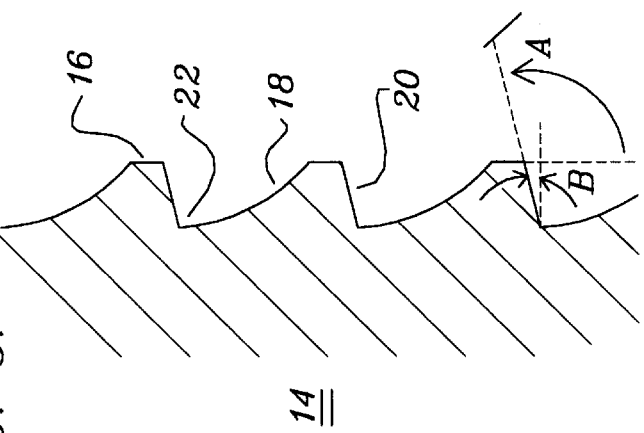
FIG. 4.
FIG. 5.
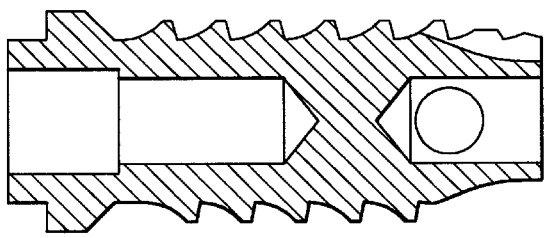
FIG. 3.
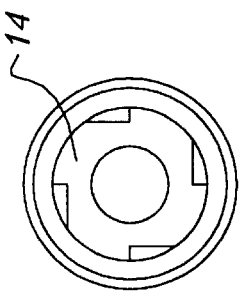
FIG. 1. PRIOR ART
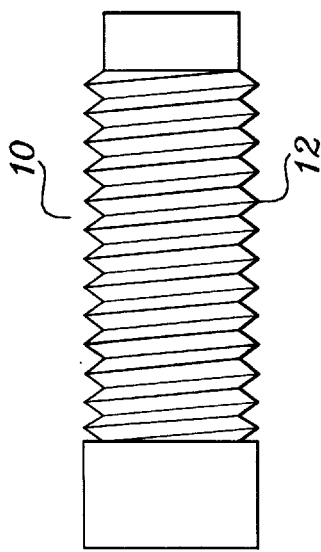
FIG. 2.

BUTTRESS THREAD IMPLANT

REFERENCE TO DISCLOSURE DOCUMENTS

The subject matter of the present application relates to Disclosure Document Number 274,554, recorded Feb. 20, 1991, and Disclosure Document Number 334,345, recorded Jul. 1, 1993.

BACKGROUND OF THE INVENTION

The present invention relates to the external configuration or a dental implant element and, more particularly, to a specific beneficial screw-like geometry for use with such an implant.

The prior art of dental implants has generally related to the use of forty pitch threading (0.025 inches between threads) having an essentially symmetric bevel as between the upper and lower faces on either side of the major thread diameters of the threading of such implant; elements. In such symmetry, the standard total included angle at the so-called bevel surface at the outer geometry of the major thread diameter has, historically, comprised an angle of about sixty degrees. Therein the distance between threads was generally equal to the thread depths. See FIG. 1.

The within inventor has discovered that a screw-like implant surface of the above type is not optimal from an anatomical perspective. More particularly, the inventor has, as a result of extended experimentation in the subject area, determined that the so-called spongy layer of bone, of which the upper and lower human mandible is formed, does not optimally engage threaded implant surfaces having a forty pitch and greater thread characteristic. The inventor has also discovered that the prior art symmetric bevel is not nearly as effective as would be an asymmetric upper-to-lower face configuration, as is more particularly set forth below.

As a consequence of the above limitations in the prior art, dental implants in the human mandible are prone to movement and loosening over time, particularly as the cumulative effect of the thousands of micro-forces, torques, stresses and strains at the bone implant interface occur. It is in response to these well known shortcomings in the prior art that the instant invention is directed.

SUMMARY OF THE INVENTION

The present inventive buttress-thread dental implant constitutes a rigid body including therein axially symmetric and radially uniform circumferential spiral pitch surfaces in the range of about 22 to about 28 or such pitch surfaces per axial inch. Above each pitch surface is a concave upper bevel surface which is longer than a lower bevel surface beneath each pitch surface. The intersection of each plane of each pitch surface with each plane of each lower bevel surface defines a total included bevel angle in the range of about 90 to about 130 degrees. The implant is also characterized by ratio of thread pitch to thread depth in the range of about 1.25:1 to about 1.40:1.

It is an object of the present invention to provide a buttress-thread dental implant having superior characteristics of gripping to the mandible bone interface and of resistance to micro-mechanical movements, stresses and the like.

It is another object to provide an improved dental implant having improved characteristics of axial and rotational stability relative to the anatomical bone interface.

It is a further object of the present invention to provide an improved dental implant surface having enhanced durability as compared to such prior art structures.

The above and other objects and advantages of the present invention will become apparent from the hereinafter set forth Brief Description of the Drawings, Detailed Description of the Invention and Claims appended herewith.

BRIEF DESCRIPTION OF THE DRAWINGS

FIG. 1 is a cross-sectional view of a prior art dental implant showing the threaded surface thereof.

FIG. 2 is an elevational view of the surface of a dental implant in accordance with the present invention.

FIG. 3 is an axial cross-sectional view of FIG. 2.

FIG. 4 is a bottom plan view of the implant of FIG. 2.

FIG. 5 is an enlarged fragmentary view of the bevel surface geometry of the invention.

DETAILED DESCRIPTION OF THE INVENTION

With reference to the view of FIG. 1 there is shown a typical prior art screw implant 10 having a plurality of radially symmetric upper and lower bevel surfaces 12. As noted in the Background of the Invention above, such prior art implants will typically have forty pitches (threads) or more to an axial inch of screw length.

The present inventive dental implant 14 is shown in the elevational view of FIG. 2, the cross sectional view of FIG. 3, the bottom view of FIG. 4 and the enlarged bevel surface view of FIG. 5.

The invention may, more particularly, be seen to comprise a so-called buttress-thread screw-like body having in the range of about twenty-two to about twenty-eight pitch surfaces 16 per inch. A preferred mode of the present invention has been determined to be about twenty-five pitches per axial inch, that is, 0.040 inches between threads.

The invention is further characterized by a particular relationship in geometry of upper bevel surface 18 to lower bevel surface 20. See particularly FIG. 5. Therein, as may be noted, the upper bevel surface is substantially longer (by a ratio of more than two to one) than lower bevel surface 20. Also, said upper surface 18 is concavely curved at a radius of about 0.040 inches, while lower bevel surface 20 is substantially flat. It is noted that in a preferred embodiment the major thread diameter, which corresponds to the location of a pitch surface 16 in FIG. 5, is 0.142 inches and the minor thread diameter 22 is about 0.112 inches. Accordingly, the difference between major and minor thread diameters, i.e., the thread depth is about 0.030 inches. Also the ratio of major-to-minor threads diameter is in the range of 1.2:1 to 1.3:1..

A further defining characteristic of the geometry of the instant dental implant is that of a first bevel angle A (see FIG. 5) which is in the range of about 90 to about 130 degrees, with 110 degrees constituting the preferred embodiment thereof. Said first bevel angle A is defined by the intersections between each pitch surface 16 and each lower bevel surface 20.

Another defining angulation of the invention is that of second bevel angle B which is the angle of lower bevel surface 20 relative to a transverse radial cross-section of the implant 14. This angle is in the range of about 20 to about 30 degrees.

It is also noted that the ratio of major-to-minor thread pitch, that is, the distance between successive pitch surfaces 16 and thread depth (as defined by minor thread diameter 22) is in the range of 1.25:1 to 1.40:1. This relationship differs materially from prior art ratios (see FIG. 1) in which the ratio of thread pitch to thread depth is approximately 1 to 1.

It has been found that the above combination of pitches per axial length, ratio of lengths of upper-to-lower bevel surfaces, and said total included bevel angle A, produce a resultant dental implant having far superior anatomical compatibility and durability than prior art dental implants. There is, as such, obtained an implant having substantial resistance to micro-mechanical axial, rotational and other movements resultant from forces, stresses and strains which are typically encountered, over time, by the implant.

It is noted that the axial face of each bevel surface 16 (the major thread diameter) is in a preferred embodiment, flattened and will have a flat axial surface of about 0.001 inch.

It is also noted that a dental implant in accordance with the present invention may be provided with any type of head. Also, the implant may be self-tapping.

It is yet further noted that an implant of the instant type may be advantageously used as a bone screw in orthopedic applications.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

Having thus described my invention what I claim as new, useful and non-obvious and, accordingly, secure by Letters Patent of the United States is:

1. A bone implant, comprising:
a rigid body having therein axially symmetric and radially uniform circumferential spiral pitch surfaces, in the range of about 22 to about 28 of said pitch surfaces per axial inch, an upper concave bevel surface above each pitch surface which is longer than a lower bevel surface beneath each pitch surface, and each intersection of each plane of each pitch surface and each plane of each lower bevel surfaces defining a total included angle in the range of about 90 to about 130 degrees, said body having minor thread diameters at intersections of said upper and lower bevel surfaces, said spiral pitch surfaces and said minor thread diameters defining a ratio of thread pitch to thread depth in the range of about 1.25:1 to about 1.40:1.

2. The implant as recited in claim 1 in which each of said lower bevel surface defines a total included angle in the range of about 20 to about 30 degrees relative to a transverse radial cross-section of said implant at each minor thread diameter thereof.

3. The implant as recited in claim 2 in which said pitch surfaces comprises a ratio of a major thread diameter to said minor thread diameter in the range of about 1.2:1 to about 1.3:1.

4. The implant as recited in claim 3 in which a difference between major and minor thread diameters comprises about 0.030 inches.

5. The implant as recited in claim 2 in which said total included angle comprises about 110 degrees.

6. The implant as recited in claim 2 in which the length of said upper concave bevel surface is about twice the length of said lower bevel surface.

7. The implant as recited in claim 6 in which said upper bevel surface defines a radius of about 0.040 inches.

8. The implant as recited in claim 2, in which said lower bevel surface comprise substantially flat surfaces.

9. The implant as recited in claim 2, in which said concave upper bevel surfaces of said pitch surfaces each define a radium in a range of about 0.040 inches.

10. The implant as recited in claim 1 comprising a buttress-thread dental implant.

11. The implant as recited in claim 1 comprising an orthopedic screw.

\* \* \* \* \*